US012011202B2

United States Patent
Johnson et al.

(10) Patent No.: US 12,011,202 B2
(45) Date of Patent: Jun. 18, 2024

(54) SURGICAL ROBOTIC SYSTEMS FOR BENDING SURGICAL RODS, AND RELATED METHODS AND DEVICES

(71) Applicant: GLOBUS MEDICAL, INC., Audubon, PA (US)

(72) Inventors: Norbert Johnson, North Andover, MA (US); Sritam Parashar Rout, Dracut, MA (US); Weston Healy, Cambridge, MA (US); David Cleary, Somerville, MA (US); Olivier Chappuis, Lutry (CH)

(73) Assignee: Globus Medical Inc., Audubon, PA (US)

( * ) Notice: Subject to any disclaimer, the term of this patent is extended or adjusted under 35 U.S.C. 154(b) by 796 days.

(21) Appl. No.: 17/128,660

(22) Filed: Dec. 21, 2020

(65) Prior Publication Data

US 2021/0106371 A1     Apr. 15, 2021

Related U.S. Application Data

(63) Continuation of application No. 16/183,980, filed on Nov. 8, 2018, now Pat. No. 10,898,252.
(Continued)

(51) Int. Cl.
*A61B 17/88*      (2006.01)
*A61B 17/70*      (2006.01)
(Continued)

(52) U.S. Cl.
CPC ...... *A61B 17/8863* (2013.01); *A61B 17/7011* (2013.01); *A61B 17/7013* (2013.01);
(Continued)

(58) Field of Classification Search
CPC ............ A61B 17/8863; A61B 17/7011; A61B 17/7013; A61B 34/30; A61B 2034/2055; A61B 2017/564
(Continued)

(56) References Cited

U.S. PATENT DOCUMENTS

| 1,068,626 | A | 7/1913 | Buck |
| 4,737,038 | A | 4/1988 | Dostoomian |

(Continued)

FOREIGN PATENT DOCUMENTS

| EP | 3461444 A1 | 4/2009 |
| EP | 3344175 A1 | 7/2018 |

(Continued)

*Primary Examiner* — Eduardo C Robert
*Assistant Examiner* — David C Comstock

(57) ABSTRACT

A robotic system may include a robot base and a rod feeding subassembly coupled to the robot base that includes a feeding actuator configured to selectively move a surgical rod. The robotic system may include a brake subassembly coupled to the robot base that includes a brake actuator configured to receive the surgical rod from the rod feeding subassembly, and selectively fix a first portion of the surgical rod with respect to the brake subassembly. The robotic system may include a bending subassembly coupled to the robot base that includes a bending actuator configured to selectively rotate to engage a second portion of the surgical rod and bend the second portion of the surgical rod with respect to the first portion of the surgical rod so that the first portion and the second portion of the surgical rod define a first bend angle.

19 Claims, 14 Drawing Sheets

Related U.S. Application Data

(60) Provisional application No. 62/583,851, filed on Nov. 9, 2017.

(51) Int. Cl.
    *A61B 34/30*     (2016.01)
    *B21D 7/00*     (2006.01)
    *A61B 17/56*     (2006.01)
    *A61B 34/20*     (2016.01)

(52) U.S. Cl.
    CPC .............. *A61B 34/30* (2016.02); *B21D 7/00* (2013.01); *A61B 2017/564* (2013.01); *A61B 2034/2055* (2016.02)

(58) Field of Classification Search
    USPC .............................. 606/262; 29/34 R, 34 D
    See application file for complete search history.

(56) References Cited

U.S. PATENT DOCUMENTS

| | | |
|---|---|---|
| 4,757,710 A | 7/1988 | Haynes |
| 7,957,831 B2 * | 6/2011 | Isaacs ................. B21D 39/048 |
| | | 700/165 |
| 8,556,807 B2 | 8/2013 | Scott et al. |
| 9,005,113 B2 | 4/2015 | Scott et al. |
| 9,271,633 B2 | 3/2016 | Scott et al. |
| 9,565,997 B2 | 2/2017 | Scott et al. |
| 9,848,922 B2 | 12/2017 | Tohmeh et al. |
| 9,872,715 B2 * | 1/2018 | Crawford ................. B21D 7/12 |
| 9,962,069 B2 | 5/2018 | Scott et al. |
| 10,898,252 B2 * | 1/2021 | Johnson ............. A61B 17/7011 |
| 2006/0015030 A1 | 1/2006 | Poulin et al. |
| 2007/0238985 A1 | 10/2007 | Smith et al. |
| 2014/0311203 A1 * | 10/2014 | Crawford ................. B21D 7/08 |
| | | 72/169 |
| 2014/0316420 A1 | 10/2014 | Ballard et al. |
| 2015/0135793 A1 | 5/2015 | Plummer et al. |
| 2017/0135770 A1 | 5/2017 | Scholl et al. |
| 2017/0143426 A1 | 5/2017 | Isaacs et al. |
| 2018/0228351 A1 | 8/2018 | Scott et al. |
| 2018/0289396 A1 | 10/2018 | McGahan et al. |
| 2018/0289491 A1 | 10/2018 | McGahan et al. |
| 2018/0310993 A1 | 11/2018 | Hobeika et al. |
| 2020/0015858 A1 | 1/2020 | Paster et al. |

FOREIGN PATENT DOCUMENTS

| | | |
|---|---|---|
| JP | 2016536051 A | 11/2016 |
| WO | 2013085982 A2 | 6/2013 |
| WO | 2015195843 A2 | 12/2015 |
| WO | 2017221257 A1 | 12/2017 |

* cited by examiner

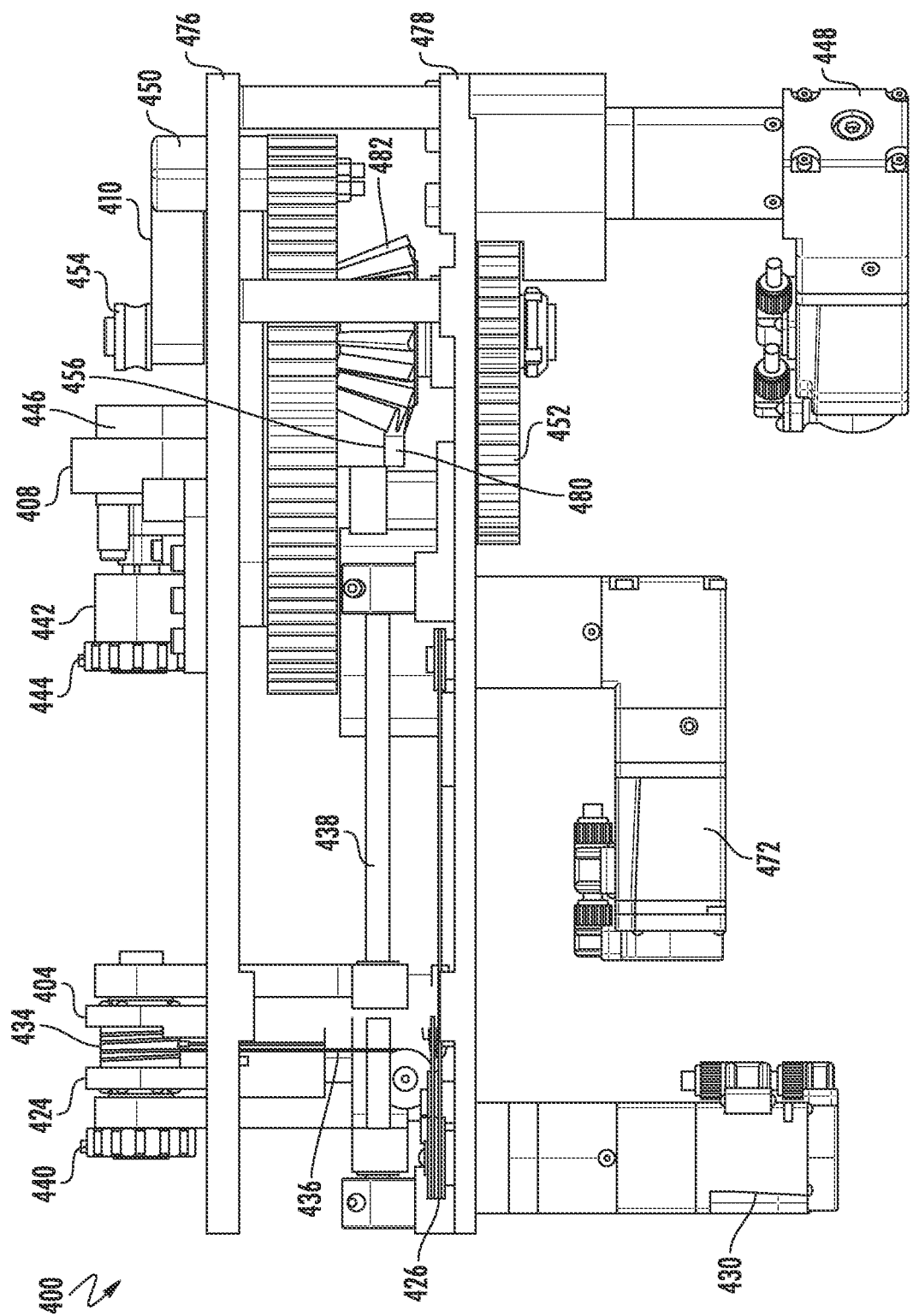

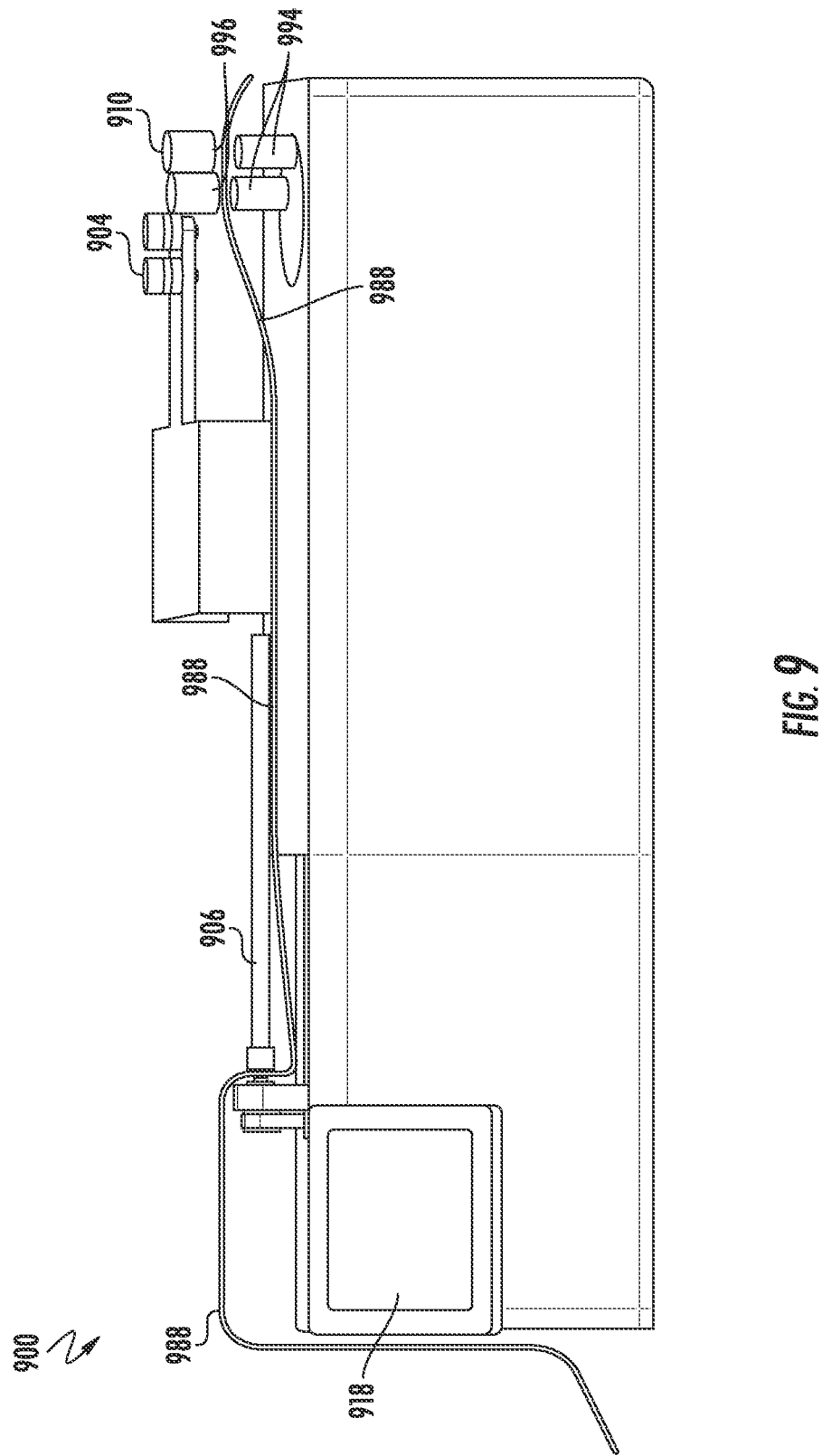

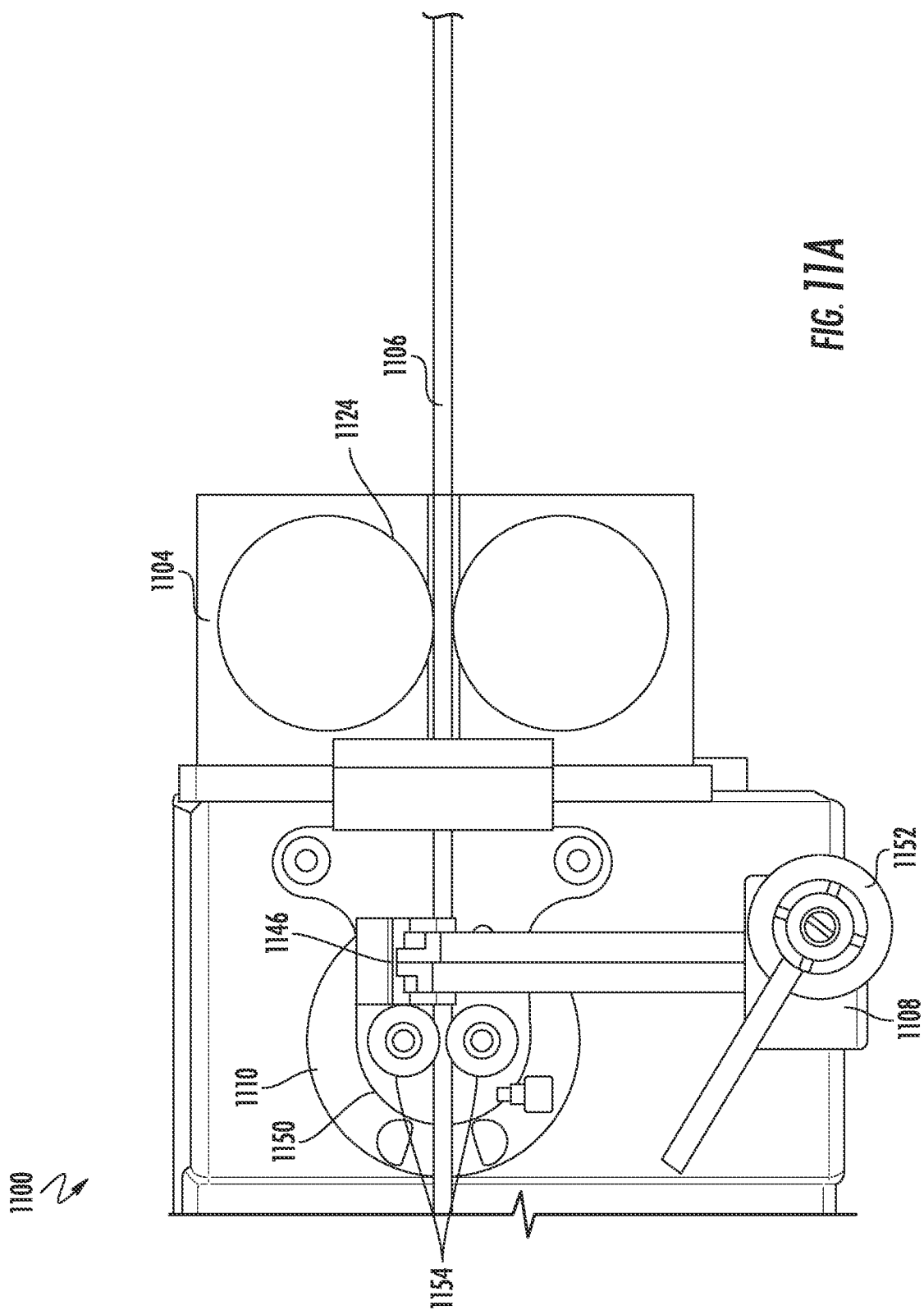

SURGICAL ROBOTIC SYSTEMS FOR BENDING SURGICAL RODS, AND RELATED METHODS AND DEVICES

This application is a continuation application of U.S. patent application Ser. No. 16/183,980 filed on Nov. 8, 2018 (published as U.S. Pat. Pub. No. 2019-0133666), which is a non-provisional application which claims priority to provisional application Ser. No. 62/583,851 filed on Nov. 9, 2017, all of which are incorporated in their entireties herein for all purposes.

FIELD

The present disclosure relates to medical devices, and more particularly, surgical robotic systems for bending surgical rods, and related methods and devices.

BACKGROUND

Spinal fusion is a surgical procedure used to correct deformity of the spine by fusing together the painful part of the spine in order to restrict its motion and relieve painful symptoms. Spinal fusion surgery is commonly utilized to treat abnormal spinal curvatures, such as scoliosis and abnormal kyphosis, for example, degenerative disc diseases, spondylolisthesis, trauma resulting in spinal nerve compression, vertebral instability caused by infections or tumors, and other conditions.

Fusion surgery may include the placement of rods and screws using instrumentation and/or the placement of bone graft in between the vertebrae. During surgery, the surgeon may correct the deformity of the spine so as to ensure that the radiographic parameters of the spine in both the sagittal and coronal plane fall within clinically accepted values. While doing so the surgeon fixes the corrected spine into place using metallic rods. The rods need to conform to the shape of the spine and hence need to be bent accordingly.

Currently, devices such as French bender and power bender are utilized in the operation room in order to bend the rods to the desired curvature. However, these devices require cumbersome manual processes to operate. In addition, use of these devices to bend the rod may also introduced notches on the rod, which may decrease the rod's fatigue life.

SUMMARY

According to some embodiments of inventive concepts, a robotic system for automatically bending a surgical rod is disclosed. The robotic system includes a robot base and a rod feeding subassembly coupled to the robot base. The rod feeding subassembly includes a feeding actuator configured to retain a surgical rod therein, and selectively move the surgical rod in a direction parallel to a longitudinal axis of the surgical rod. The robotic system further includes a brake subassembly coupled to the robot base. The brake subassembly includes a brake actuator configured to receive the surgical rod from the rod feeding subassembly, and selectively fix a first portion of the surgical rod with respect to the brake subassembly. The robotic system further includes a bending subassembly coupled to the robot base. The bending subassembly includes a bending actuator configured to selectively rotate about a first rotational axis perpendicular to the longitudinal axis of the surgical rod. Rotating the bending actuator causes the bending actuator to engage a second portion of the surgical rod and bend the second portion of the surgical rod with respect to the first portion of the surgical rod so that the first portion and the second portion of the surgical rod define a first bend angle.

According to some other embodiments of inventive concepts, a method of operating a robotic system is disclosed. The method includes selectively operating a rod feeding subassembly, including retaining a surgical rod in the rod feeding subassembly. Operating the rod feeding subassembly further includes causing a feeding actuator of the rod feeding subassembly to selectively move the surgical rod in a direction parallel to a longitudinal axis of the surgical rod. The method further includes selectively operating a brake subassembly, including receiving the surgical rod in the brake feeding subassembly from the rod feeding subassembly. Operating the brake subassembly further includes causing a brake actuator of the brake subassembly to selectively fix a first portion of the surgical rod with respect to the brake subassembly. The method further includes selectively operating a bending subassembly, including causing a bending actuator of the bending subassembly to selectively rotate about a first rotational axis perpendicular to the longitudinal axis of the surgical rod. Rotating the bending actuator causes the bending actuator to engage a second portion of the rod and bend the second portion of the rod with respect to the first portion of the surgical rod so that the first portion and the second portion of the surgical rod define a first bend angle.

Other methods and related surgical systems, and corresponding methods and computer program products according to embodiments of the inventive subject matter will be or become apparent to one with skill in the art upon review of the following drawings and detailed description. It is intended that all such surgical systems, and corresponding methods and computer program products be included within this description, be within the scope of the present inventive subject matter, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIG. 8 illustrates a side view of the components of the bending robot of FIG. 4, according to some embodiments;

FIG. 9 illustrates components of a rod feeding subassembly for a bending robot according to another alternative embodiment;

FIGS. 11A and 11B illustrate components of a bending robot according to another alternative embodiment.

DETAILED DESCRIPTION

Figure 1:
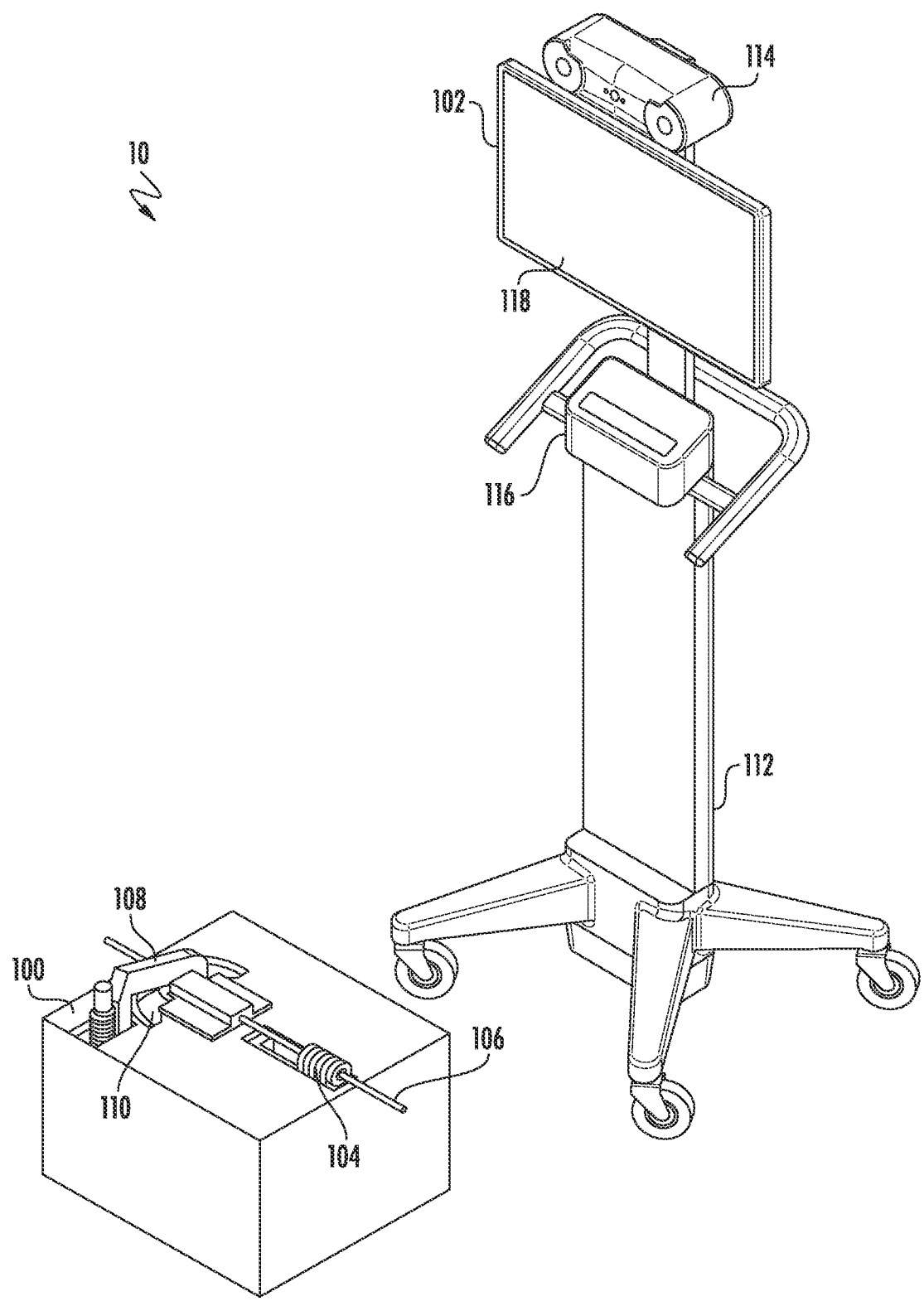
FIG. 1 illustrates a view of a robotic bending system for automatically bending a surgical rod, according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Referring now to FIG. 1, a view of a robotic bending system 10 for automatically bending a surgical rod intraoperatively is illustrated according to some embodiments. The bending system 10 of FIG. 1 includes a bending robot 100 and may also include a controller unit 102 for controlling and/or monitoring the operation of the bending robot 100 and/or other components or devices. The bending robot 100 includes a rod feeding subassembly 104 for receiving, feeding, and rotating a surgical rod 106, a brake subassembly 108 for retaining a first portion of the surgical rod 106 at a particular position, and a bending subassembly 110 for bending a second portion of the surgical rod 106 with respect to the first portion of the surgical rod 106 to define a bend angle between the first and second portions of the surgical rod 106. By feeding and rotating additional sections of the surgical rod 106, additional portions of the surgical rod can be bent to form a number of different shapes suitable for use in spinal fusion surgery or other procedures.

In this example, the controller unit 102 may include a controller base 112 and a plurality of components, which may be in communication with each other and/or components of the bending robot 100, as desired. For example, the controller unit may include a camera 114 for monitoring the bending robot and/or other aspects of the surgery or procedure, an input device 116 for receiving instructions from a user before or during the procedure, and a display device 118 for providing visual information to a user before or during the procedure. The robot 100 and/or controlled unit 102 may include one or more processor circuits (not shown) for executing machine-readable instructions to operate components of the bending robot 100 or other components or devices.

Figure 2:
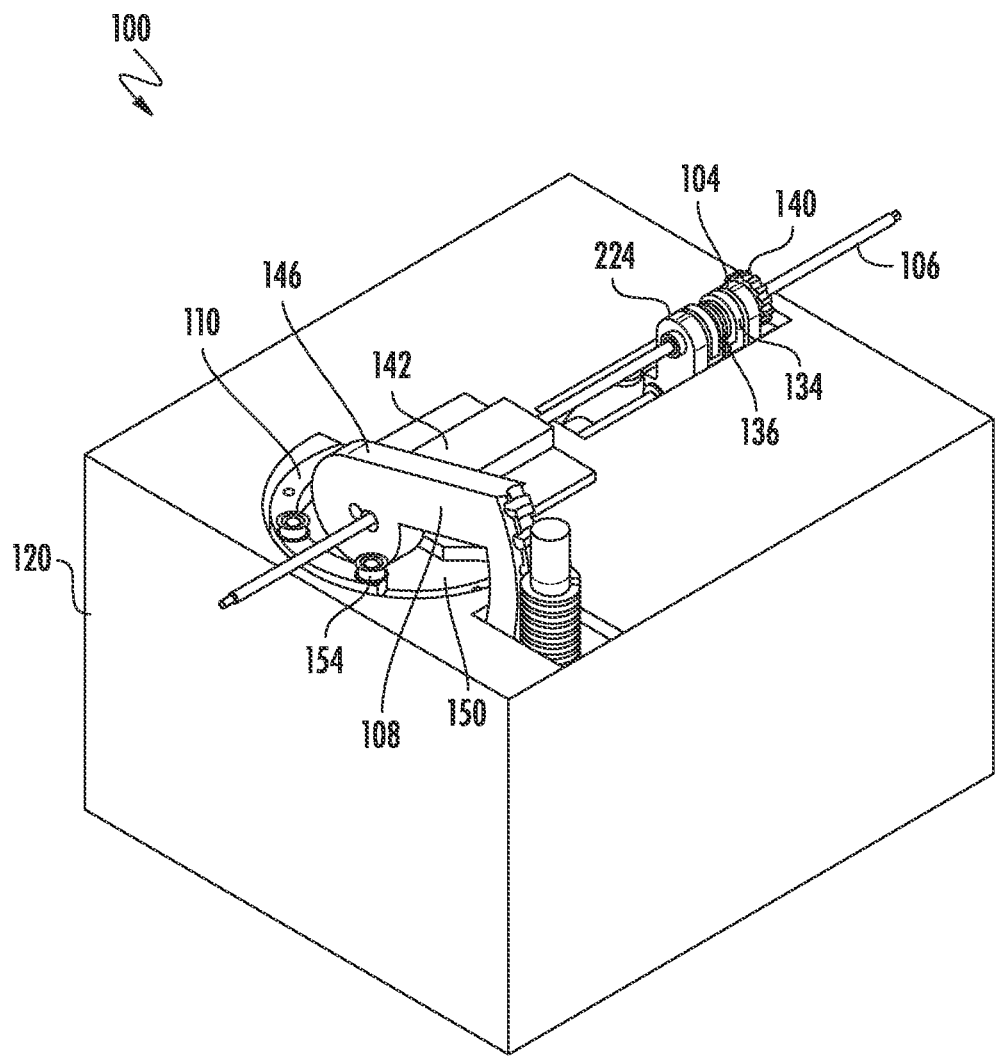
FIG. 2 illustrates a view of a bending robot of the robotic bending system of FIG. 1, according to some embodiments.

Referring now to FIG. 2, a more detailed view of the bending robot 100 of FIG. 1 is illustrated, according to some embodiments. As shown in FIG. 2, the bending robot 100 includes a robot housing 120 that is part of a robot base for housing components of the rod feeding subassembly 104, brake subassembly 108, bending subassembly 110, and other components. The rod feeding subassembly 104 includes a rod feeding actuator 124 configured to retain a surgical rod 106 therein, selectively move the surgical rod 106 in a direction parallel to a longitudinal axis of the surgical rod 106, and selectively rotate the surgical rod about the longitudinal axis of the surgical rod 106. The rod feeding actuator 124 includes an actuator spindle 134 with a pulley cable 136 wound therearound, and a retaining ring 140 for retaining and aligning the surgical rod 106. In this example, the retaining ring 140 is sized to hold the surgical rod 106 in place by friction, and to allow the rod to slide through the ring when an appropriate amount of force is applied to the surgical rod 106. The retaining ring 140 in this example may be selectively replaced with a differently sized retaining ring to accommodate a surgical rod having a different diameter. As will be discussed below, a pulley subassembly (not shown) selectively advances and rotates the surgical rod 106 to position the surgical rod 106 in a correct location and orientation with respect to the brake subassembly 108 and the bending subassembly 110. It should also be understood that, while this embodiment uses a pulley subassembly, other types of feeding actuator linkages may be used to transfer power from one or more motors to move and/or rotate the rod feeding actuator 124.

The brake subassembly 108 includes a brake housing 142 and a brake actuator 146 configured to receive the surgical rod 106 from the rod feeding subassembly 104, and selectively fix a first portion of the surgical rod 106 with respect to the brake subassembly 108. In this embodiment, after the brake actuator 146 fixes the surgical rod 106, the rod feeding subassembly 104 moves longitudinally back to its original position and may advance and/or rotate the surgical rod 106 further after the brake actuator 146 is released.

While the brake actuator 146, is engaged, the bending subassembly 110 includes a bending actuator 150 that selectively rotate about a first rotational axis perpendicular to the longitudinal axis of the surgical rod 106 to engage a second portion of the surgical rod 106 and bend the second portion of the surgical rod 106 with respect to the first portion of the surgical rod 106 so that the first portion and the second portion of the surgical rod 106 define a first bend angle. To prevent notching of the surgical rod 106 during the bending process, a pair of roller bearings 154 positioned on either side of the surgical rod 106 form the engagement points between the surgical rod 106 and the bending actuator 150 during the bending process.

Figure 3:
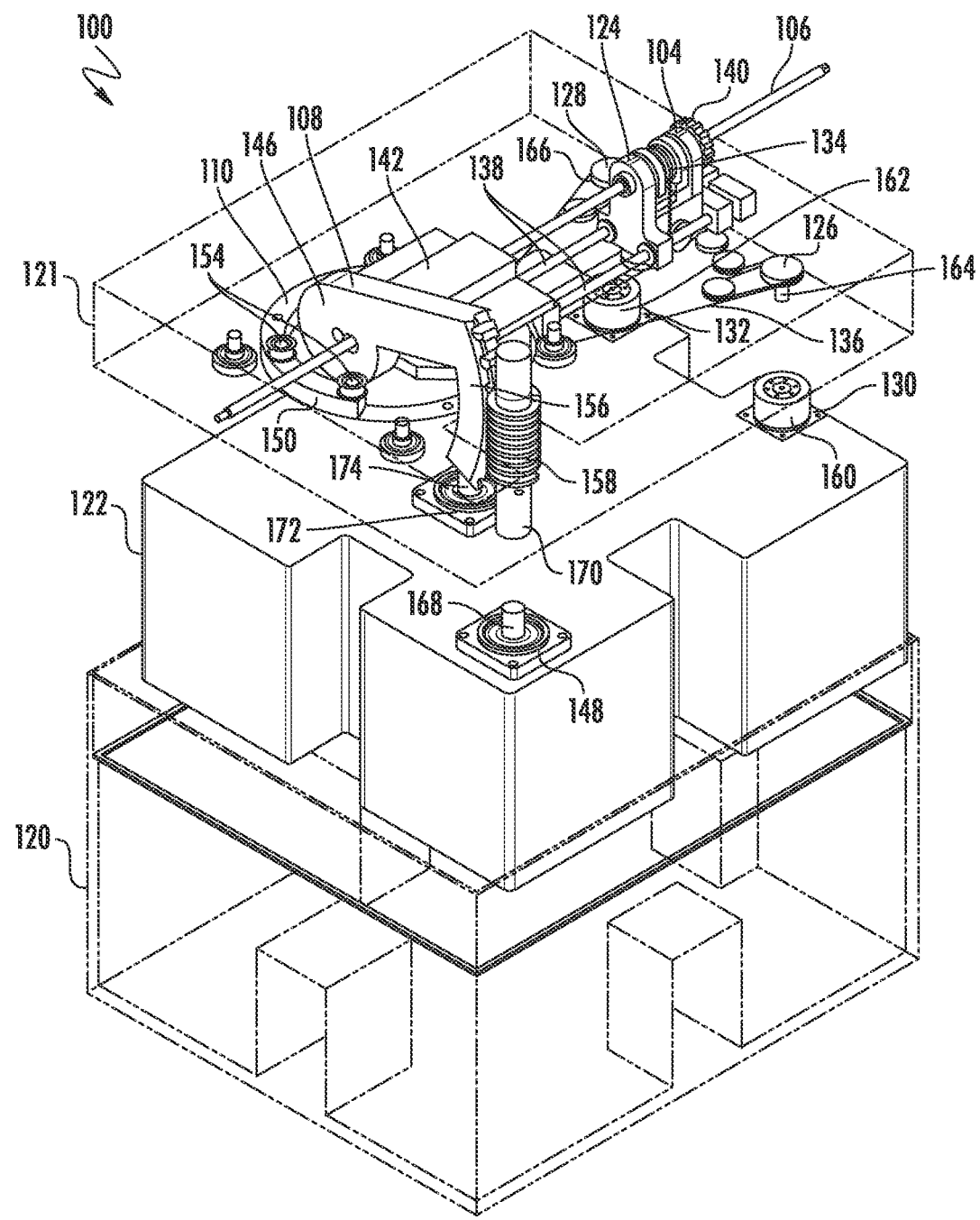
FIG. 3 illustrates a partially disassembled view of the bending robot of FIG. 2, according to some embodiments.

Referring now to FIG. 3, a partially disassembled view of the bending robot 100 of FIG. 2 is illustrated according to some embodiments. In this example, a mechanical housing 121 include mechanical components of the rod feeding subassembly 104, brake subassembly 108, and bending subassembly 110, and a motor housing 122 includes additional components of the bending robot 100, including a first feeding actuator motor 130, a second feeding actuator motor 132, a brake actuator motor 148, a bending actuator motor 172, and/or additional internal mechanical and/electrical components such as additional linkages and/or electronic processor circuits or other circuits. For example, in some examples a memory coupled to a processor circuit may include machine-readable instructions that, when executed by the processor circuit, cause the processor circuit to cause the rod feeding subassembly 104 to selectively move the surgical rod and selectively rotate the surgical rod 106, cause the brake subassembly 108 to selectively fix the first portion of the surgical rod, and/or cause the bending subassembly 110 to selectively rotate about the first rotational axis to engage the second portion of the surgical rod 106 and bend the second portion of the surgical rod with 106 respect to the first portion of the surgical rod 106.

The mechanical housing 121 is configured to be removably coupled to the motor housing 122 so that the first and second feeding actuator motors 130, 132, brake actuator motor 148, and bending actuator motor 172 can selectively operate the rod feeding subassembly 104, brake subassembly 108, and bending subassembly 110, respectively. In this example, the mechanical housing 121 does not include any electrical or electronic components that could be damaged by conventional preoperative or intraoperative sterilization techniques, such as autoclaving, high-temperature steam sterilization, chemical sterilization, or other techniques. Thus, by disposing the non-sterile motor housing 122 in the sterile robot housing 120, and removably coupling the sterile mechanical housing 121 onto the motor housing 122, intraoperative sterility can be maintained without needing to expose the electrical and/or electronic components of the bending robot 100 to harsh sterilization techniques that may damage these components and may reduce the useful life of these components.

As shown in FIG. 3, the rod feeding subassembly includes a first pulley subassembly 126 configured to engage and be driven by the first feeding actuator motor 130, and a second pulley subassembly 128 configured to engage and be driven by the second feeding actuator motor 132. A pulley cable 136 is wound around first pulley subassembly 126 and the second pulley subassembly 128, as well as the actuator spindle 134 of the rod feeding actuator 124. The first pulley subassembly 126 includes a first pulley transmission input 160 that matingly engages with a first pulley transmission output 164 that is driven by the first feeding actuator motor 130. The first pulley subassembly 126 also includes a second pulley transmission input 162 that matingly engages with a second pulley transmission output 166 that is driven by the second feeding actuator motor 132.

In this embodiment, the directions of rotation of the first feeding actuator motor 130 and the second feeding actuator motor 132 determine the direction or movement and/or rotation of the surgical rod 106. For example, to move the rod feeding actuator 124 in a longitudinal direction along a longitudinal rail subassembly 138 toward the brake subassembly 108 and bending subassembly 110, the first feeding actuator motor 130 rotates counterclockwise and the second feeding actuator motor 132 rotates clockwise. Similarly, to move the rod feeding actuator 124 in a longitudinal direction along the longitudinal rail subassembly 138 away from the brake subassembly 108 and bending subassembly 110, the first feeding actuator motor 130 rotates clockwise and the second feeding actuator motor 132 rotates counterclockwise. To rotate the actuator spindle 134 in a clockwise direction, the first feeding actuator motor 130 rotates clockwise and the second feeding actuator motor 132 also rotates clockwise. To rotate the actuator spindle 134 in a counterclockwise direction, the first feeding actuator motor 130 rotates counterclockwise and the second feeding actuator motor 132 also rotates counterclockwise.

The brake actuator 146 is configured to engage and be driven by the brake actuator motor 148. The brake actuator 146 includes a worm gear 158 having a brake transmission input 168 that matingly engages with a brake transmission output 170 that is driven by the brake actuator motor 148. Driving the worm gear 158 causes a brake gear arm 156 to engage and/or disengage the brake actuator 146 to selectively fix or release the surgical rod 106. In this example, selective operation of the brake actuator motor 148 in a first rotational direction when the brake actuator 146 is in a neutral position causes the brake gear arm 156 to move the brake actuator 146 from the neutral position to an engaged position to selectively fix the first portion of the surgical rod 106 with respect to the brake subassembly 108. Similarly, selective operation of the brake actuator motor 148 in a second rotational direction opposite the first rotational direction when the brake actuator 146 is in the engaged position causes the brake gear arm 156 to move the brake actuator 146 from the engaged position to the neutral position to selectively release the surgical rod 106. In this example, the brake subassembly 108 is a brake and cutting subassembly that further includes an internal blade mechanism (not shown), wherein selective operation of the brake actuator motor 148 in the second rotational direction when the brake actuator 146 is in the neutral position causes a blade of the internal blade mechanism to cut the surgical rod 106. In this example, two internal plates may be slid apart in a reverse scissoring motion, introducing tension to the rod in two different directions and trimming the excess. It should also be understood that an alternative or additional brake actuator linkage may be used in place of or in addition to the worm gear 158 and brake gear arm 156 of the brake subassembly 108.

Similar to the rod feeding subassembly 104 and the brake subassembly 108, the bending actuator 150 of bending subassembly 110 includes a bending transmission input (not shown) that matingly engages with a bending transmission output 174 that is driven by the bending actuator motor 172, and that transfers power from the bending actuator motor 172 through a bending actuator linkage (not shown) to drive the bending actuator 150. Thus, when the sterile mechanical housing 121 is removably coupled to the motor housing 122 in the sterile robot housing 120, the bending robot 100 is able to automatically bend the surgical rod 106 in real-time in a sterile, intraoperative environment. Following each bend, the previously fixed portion of the surgical rod 106 may be advanced and/or rotated by the rod feeding subassembly 104 and another portion may be fixed by the brake subassembly 108. The bending subassembly 110 then bends the previously fixed portion of the surgical rod 106, and so on, until the rod is bent to a desired shape and can be cut and used as part of the spinal fusion surgery or other procedure.

Figure 4:
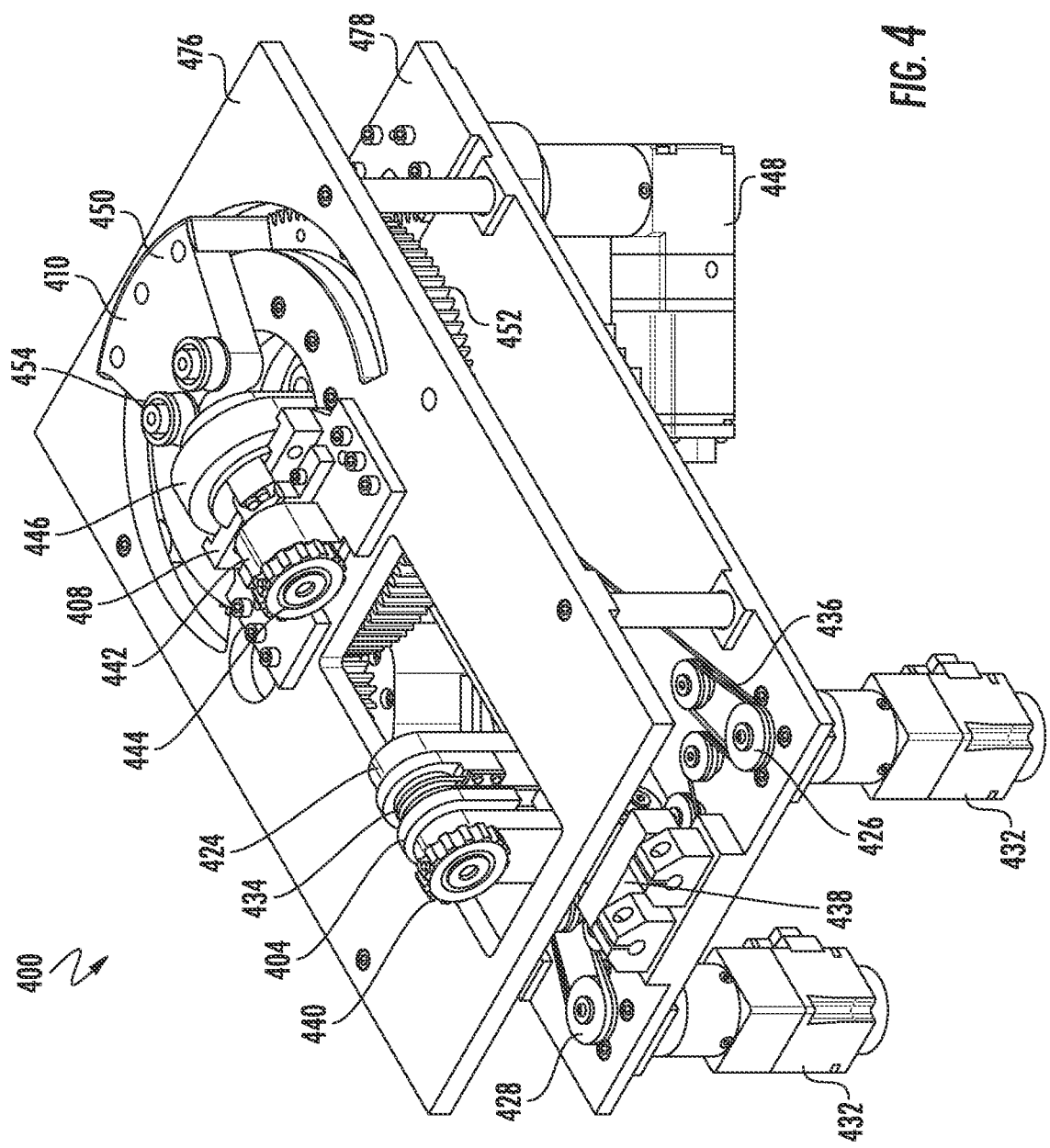
FIG. 4 illustrates an internal view of components of a bending robot according to an alternative embodiment.
Figure 5:
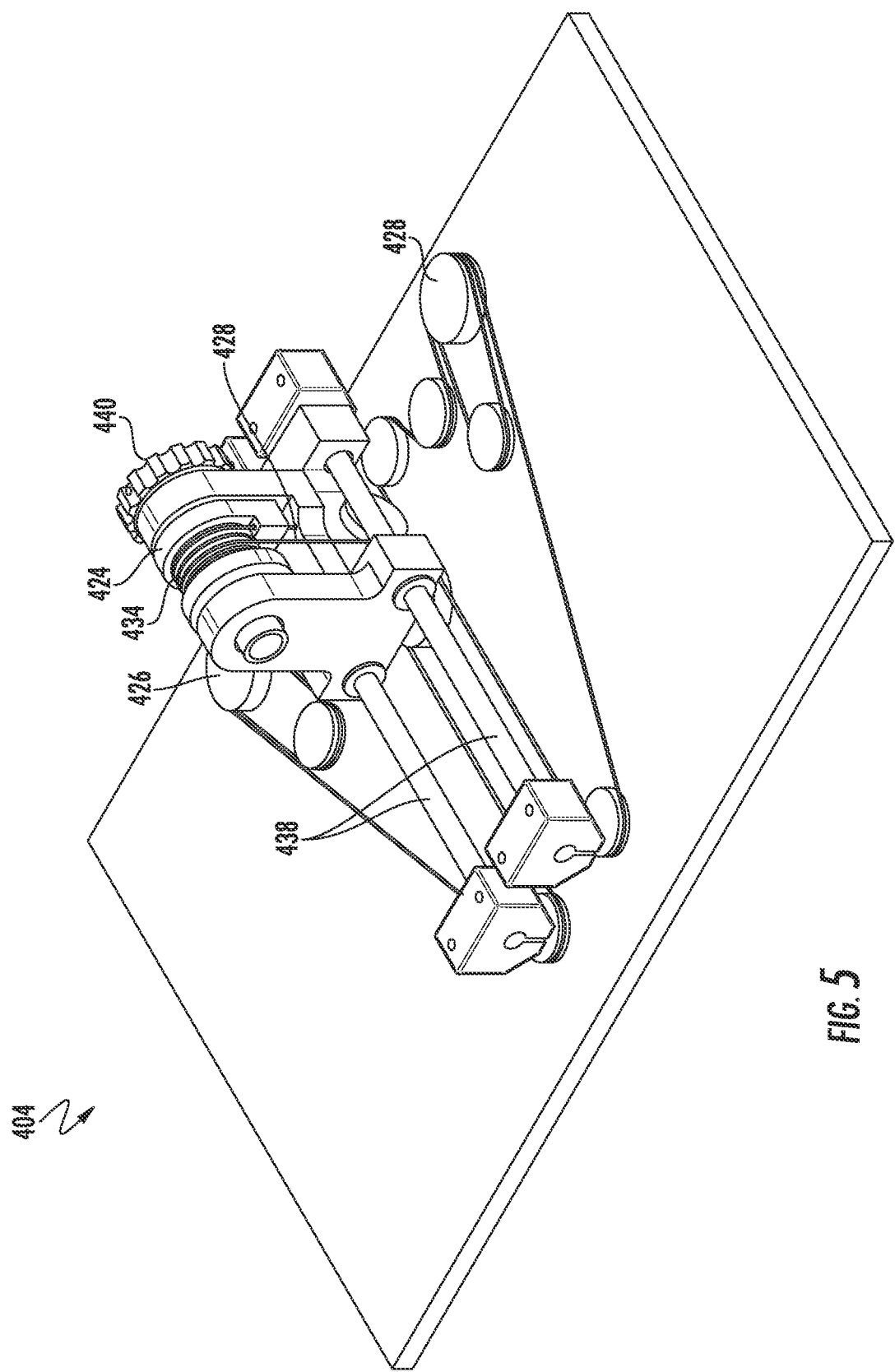
FIG. 5 illustrates components of a rod feeding subassembly of the bending robot of FIG. 4, according to some embodiments.

Referring now to FIGS. 4-7, components of a bending robot 400 according to an alternative embodiment are illustrated. As shown by FIG. 4, the bending robot 400 in this embodiment includes a rod feeding subassembly 404, a brake and cutting subassembly 408, and a bending subassembly 410. As shown by FIGS. 4, and 5, the rod feeding subassembly 404 includes a rod feeding actuator 424 that is selectively longitudinally movable and rotatable via a first pulley subassembly 426 and second pulley subassembly 428. A first feeding actuator motor 430 and a second feeding actuator motor 432 transfer power through the first pulley subassembly 426 and second pulley subassembly 428 via a pulley cable 436 to move the actuator spindle 434 along a longitudinal rail subassembly 438 and rotate the actuator spindle. The actuator spindle 434 includes a removable retaining ring 440 for retaining and aligning the surgical rod (not shown) therein.

Figure 6:
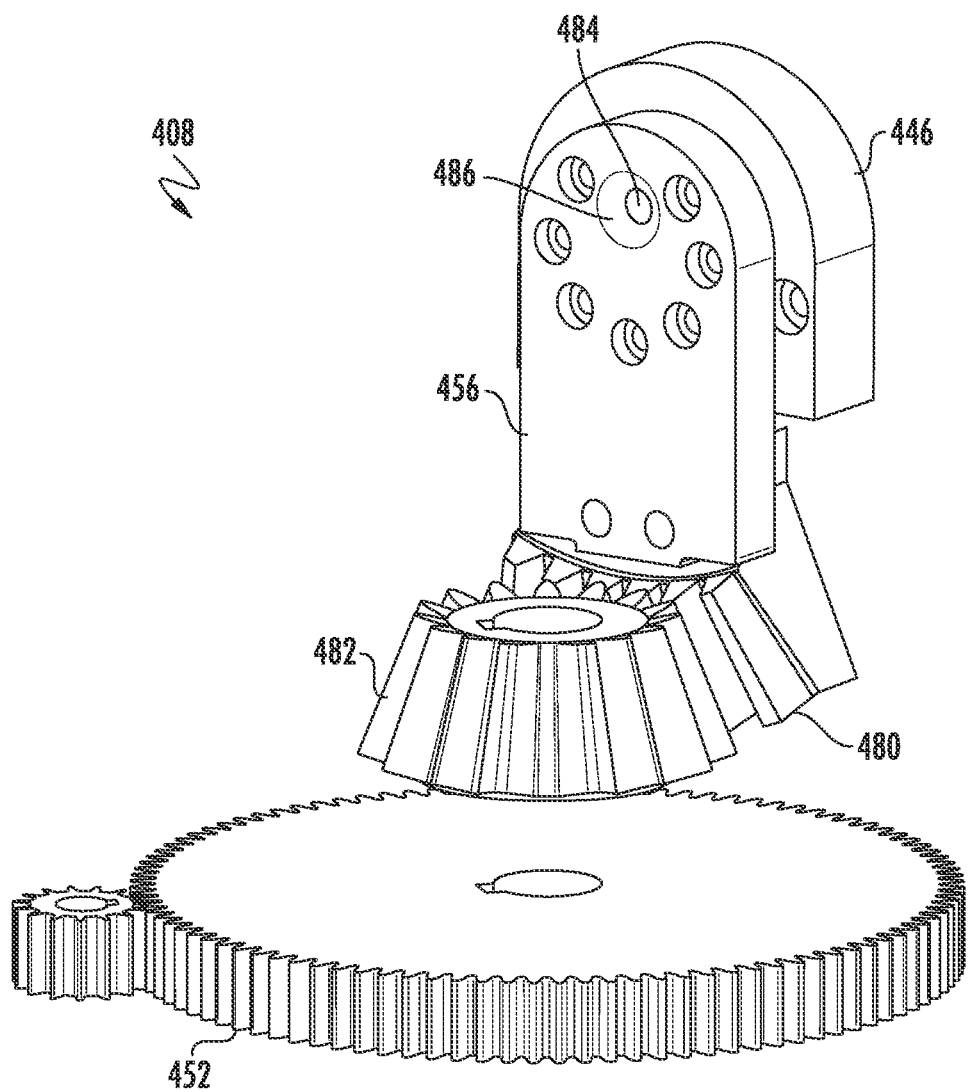
FIG. 6 illustrates components of a brake and cutting subassembly of the bending robot of FIG. 4, according to some embodiments.

As shown by FIG. 4, the brake and cutting subassembly 408 includes a brake housing 442 having a retaining ring 444 similar to the retaining ring 440 of the rod feeding subassembly 404, for receiving and aligning the surgical rod. A brake actuator 448 is controlled by a brake actuator motor 448 to selectively fix and/or release the surgical rod. As shown by FIG. 6, the brake actuator 446 includes a brake gear subassembly including a brake gear 482. In this example, the brake gear is coaxial with, but independently rotatable with respect to, the main gear of the bending gear subassembly 452. This arrangement is to conserve internal space, but it should be understood that other mechanical arrangements may be used to achieve the same or similar functionality. In this example, rotating the brake gear 482 causes the brake gear arm 456 to rotate in a first direction from a neutral position, wherein the surgical rod can be freely moved and rotated with respect to through-hole 484, to an engaged position, wherein the brake gear arm rotates to compress the surgical rod within the through-hole and fix the surgical rod in place. In this embodiment, rotating the brake arm from the neutral position in an opposite direction causes a blade of an internal blade mechanism (not shown) to cut the surgical rod.

Figure 7:
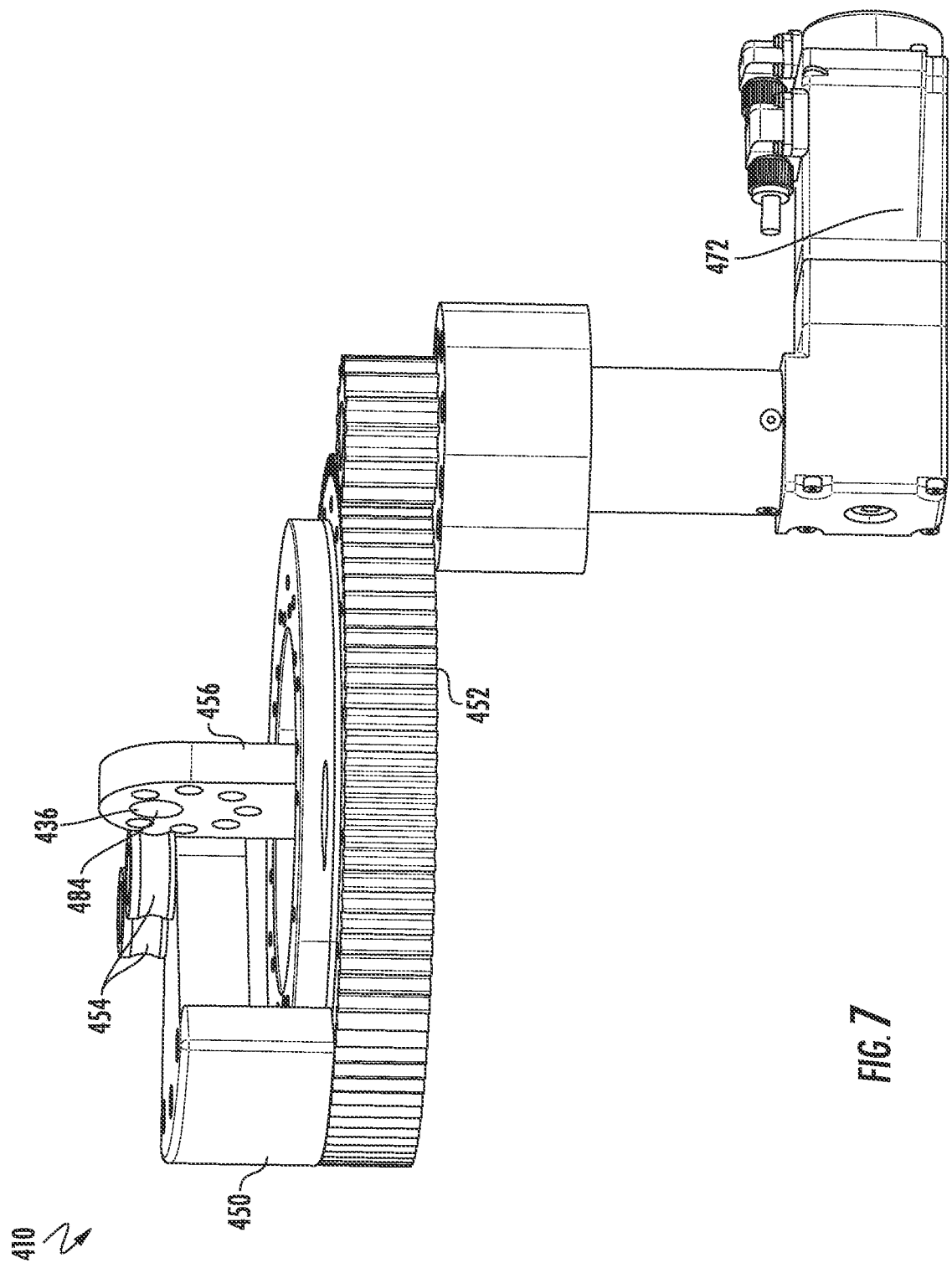
FIG. 7 illustrates components of a bending subassembly of the bending robot of FIG. 4, according to some embodiments.

Referring now to FIG. 7, the bending subassembly 410 includes a bending actuator 450 controlled by a bending actuator motor 472 via a bending gear subassembly 452. A pair of roller bearings 454 are configured to engage the surgical rod when the bending actuator 450 is rotated to bend the surgical rod to a predetermined bend angle.

FIG. 8 illustrates a side view of the components of the bending robot 400 of FIG. 4. As shown by FIG. 8, the components of the bending robot 400 in this example are coupled to an upper support structure 476 and a lower support structure 478 coupled to and spaced apart from the upper support structure 476, to provide structural support for the components of the bending robot 400 while allowing for easier access to the components of the bending robot 400 for maintenance and repair, for example.

Many techniques are available for sterilizing and preventing contamination of a surgical rod being bent in an intraoperative environment. For example, the embodiment of FIGS. 2 and 3 includes a removable mechanical housing 121 that can be completely sterilized using conventional sterilization techniques without risking damage to the electrical or other components of the separate motor housing 122. In another example illustrated in FIG. 9, a bending robot 900 includes a rod feeding subassembly 904 and a bending subassembly 910 for feeding, rotating and bending a surgical rod 906. In this example, the bending robot 900 includes integrated computing components, including an integrated display 918, for controlling the bending robot 900.

In the embodiment of FIG. 9, a sterile drape 988 may cover the non-sterilized components of the bending robot 400, with sterilized components being coupled to the non-sterilized components via magnetic connectors 990, 994 of the sterilized components matingly coupling to complementary magnetic connectors 992, 996 (e.g., male-female connections) of the non-sterilized components, with motion of the components being transferred through the drape 988. While magnetic connections are used in this embodiment, it should be understood that other connections, such as a tight-fit mechanism that allows for transferring mechanical motion without compromising the integrity of the drape 988, may be used. For example, in this and other embodiments, the rotatable components do not require a range of motion of more than 180 degrees. Because of this relatively small range of rotation, using a tight fit mechanism is possible without tearing or otherwise unduly straining the drape 988.

Figure 10A:
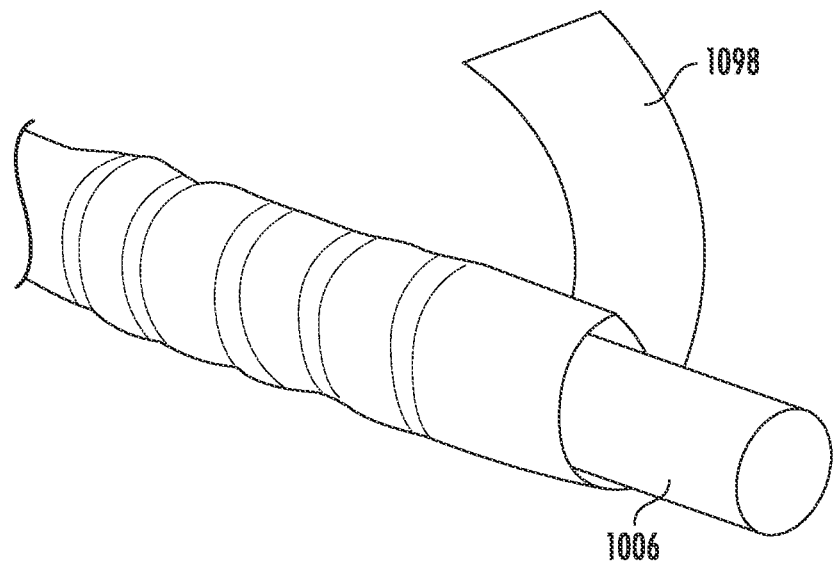
FIGS. 10A-D illustrate surgical rods having removable sterile sleeves, according to some embodiments.

In some embodiments, a sterile surgical rod may be sealed within a sterile sleeve or wrap, which is then bent intraoperatively in a non-sterile environment. In this regard, FIGS. 10A-D illustrate surgical rods having removable sterile sleeves as illustrated, according to some embodiments. Referring to FIG. 10A, a sterile surgical rod 1006 is wrapped in a spiral sterile wrap 1098 material. Following bending of the surgical rod 1006, the spiral sterile wrap 1098 may be removed and the sterile surgical rod 1006 may be delivered into the sterile intraoperative environment.

Figure 10B:
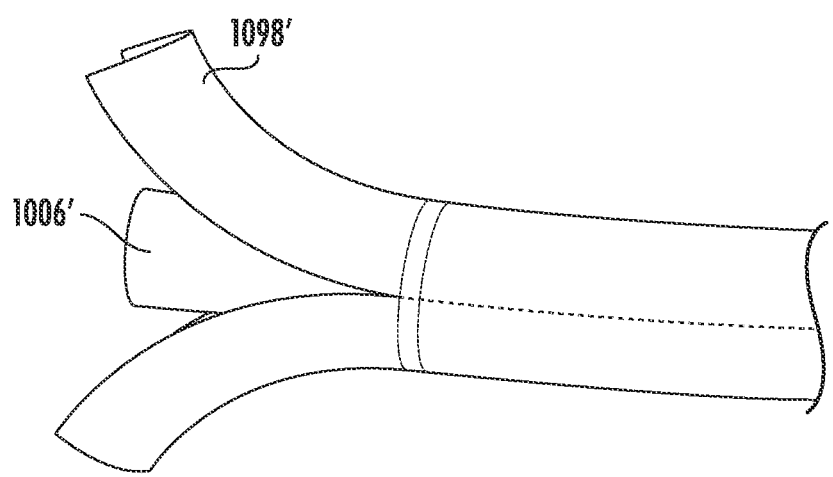
Figure 10C:
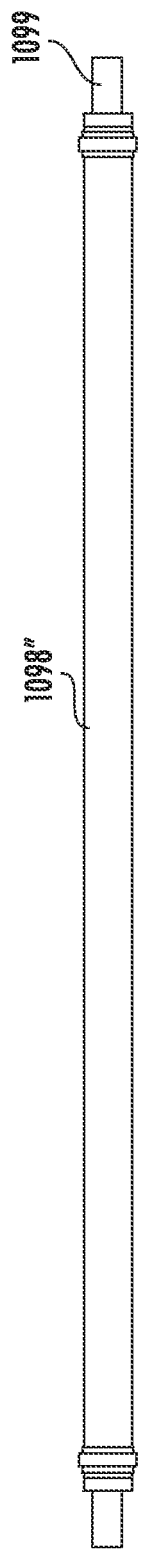
Figure 10D:
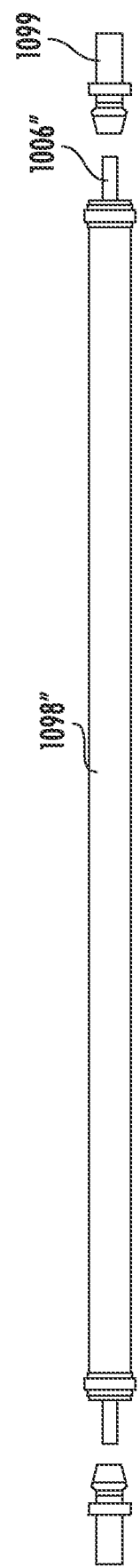

Similarly, FIG. 10B illustrates another sterile surgical rod 1006' having a sterile sleeve 1098' that may be peeled away from the sterile surgical rod 1006' following bending of the sterile surgical rod 1006'. FIGS. 10C and 10D illustrate a sterile surgical rod 1006" disposed in a sterile flexible shaft 1098", which is sealed at either end by removable caps 1099. A bending robot in a non-sterile environment may be configured to bend the flexible shaft 1098", thereby bending the sterile surgical rod 1006" within the flexible shaft 1098" without contacting or contaminating the sterile surgical rod 1006".

Following the bending process, the sterile surgical rod 1006" may be removed from the flexible shaft 1098" and delivered into the sterile intraoperative environment. In these and other embodiments, the coverings for the sterile surgical rods 1006, 1006', 1006" may have a uniform outer diameter, so that different surgical rod diameters may be used without the need for a bending robot to adjust to different outside diameters of the respective coverings.

Figure 11B:
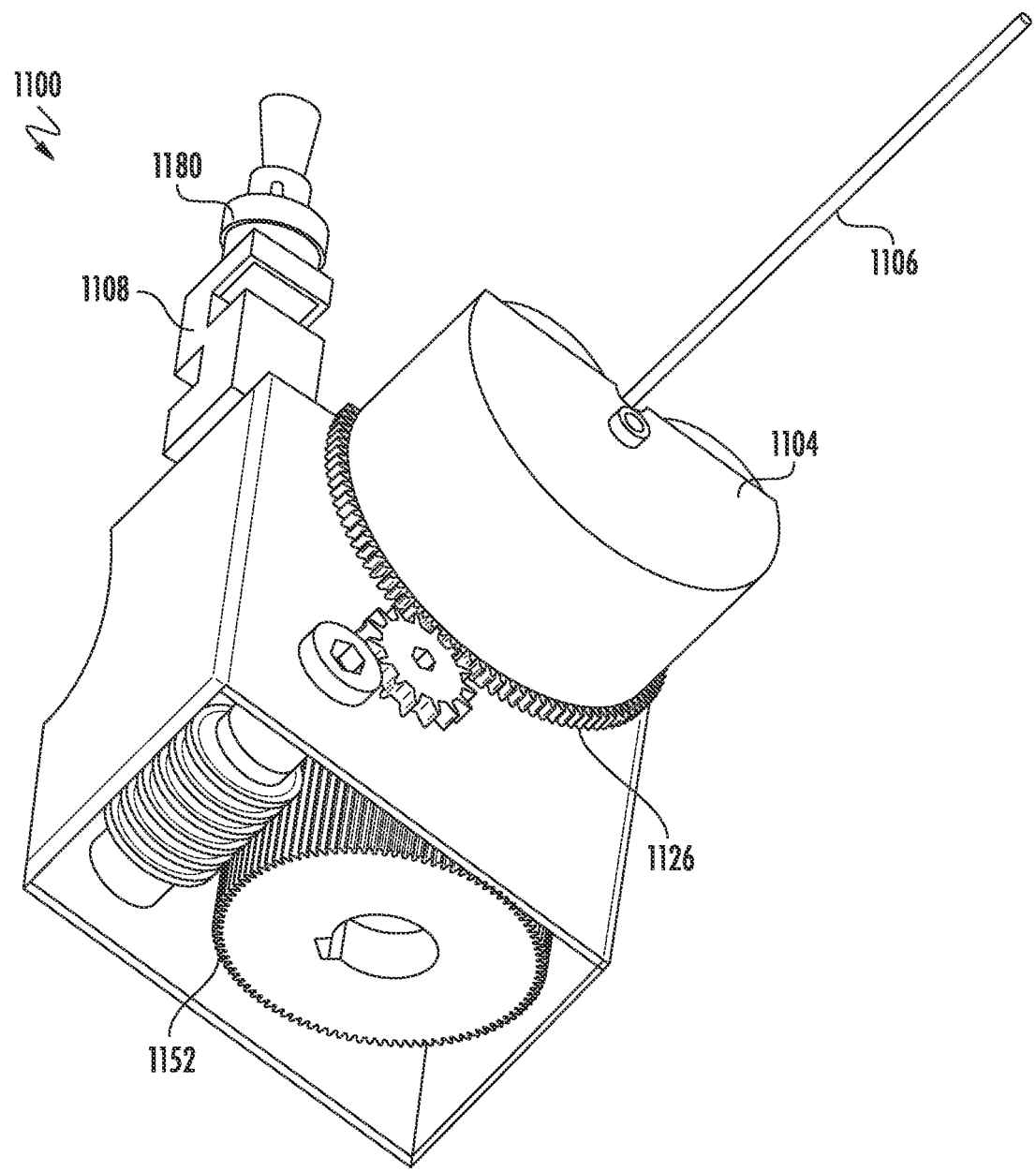

FIGS. 11A and 11B illustrate components of a bending robot 1100 according to another alternative embodiment. The bending robot 1100 in this embodiment includes a rod feeding subassembly 1104 including a rod feeding actuator 1124, a brake subassembly 1108 with a brake actuator 1146 having an integrated marking mechanism, and bending subassembly 1110 having a bending actuator 1150 including a pair of roller bearings 1154 for engaging and bending the surgical rod 1106 without notching or otherwise damaging the surgical rod 1106.

In this example, the rod feeding actuator 1124 is controlled via a feeding gear mechanism 1126, and the bending actuator 1150 is controlled via a bending gear subassembly 1152. The brake actuator 1146 is controlled by a manual clamp mechanism 1180 in this embodiment. An integrated marking mechanism, e.g., a retractable marker, may mark points on the rod which, once marked, dictate the shape of the rod as needed to correct an injury, where the marked points indicate the points of the screws along the curve of the bend. This allows for additional control over the shape of the rod, and marking ensures that the surgeon is aware entirely of which screws the rod aligns with for a spinal fusion or other procedure. Alternatively, the surgical rod could be pre-marked, e.g., every five millimeters, with a corresponding number. By displaying these numbers on the screen of a monitor viewable by the surgeon during the procedure, the surgeon can ensure proper positioning of the rods.

Figure 12:
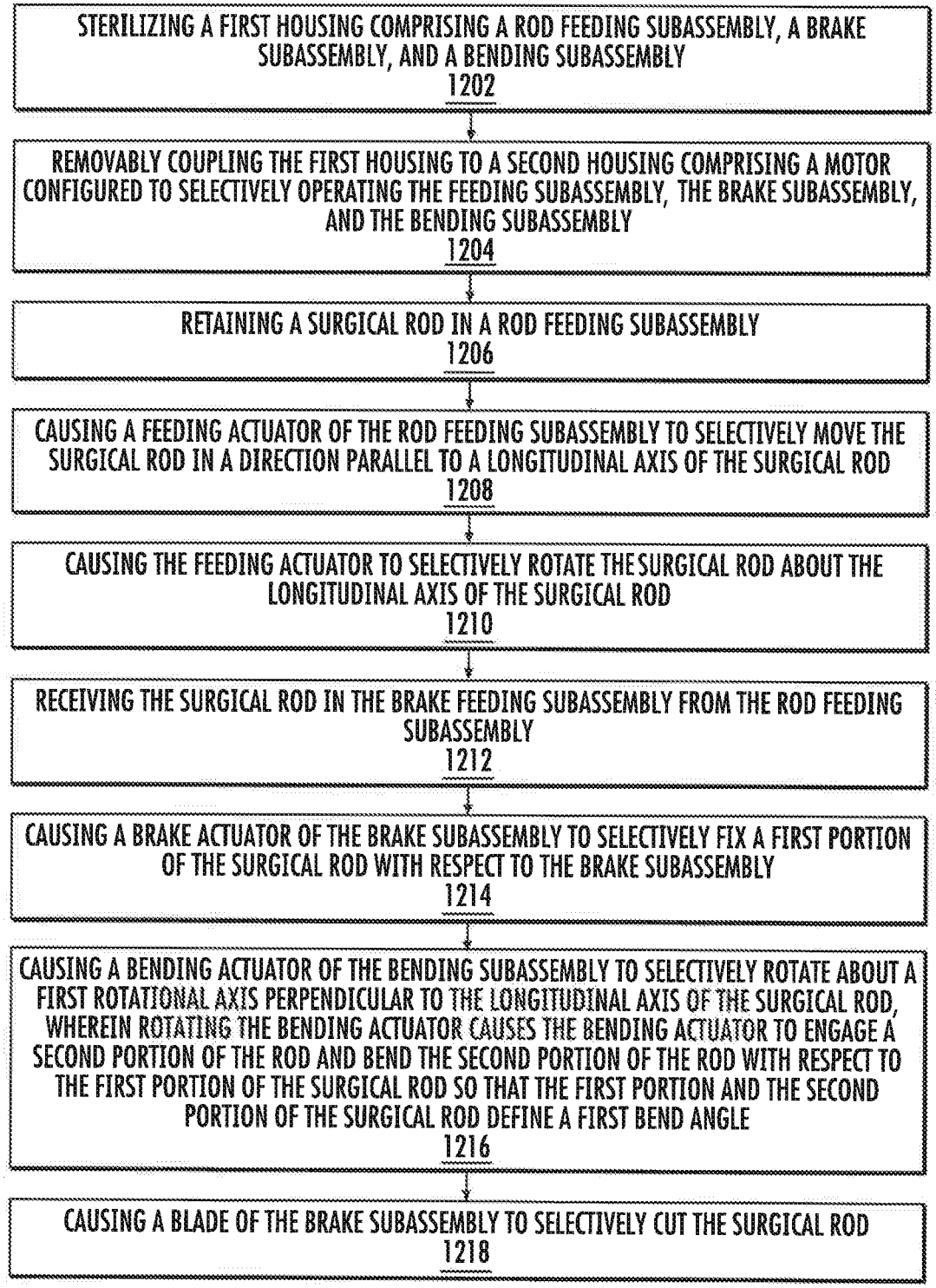
FIG. 12 is a flowchart of a method of operating a bending robot, according to some embodiment.

FIG. 12 is a flowchart of operations 1200 for operating a bending robot, according to some embodiments. The operations 1200 include sterilizing a first housing including a rod feeding subassembly, a brake subassembly, and a bending subassembly (Block 1202), and removably coupling the first housing to a second housing including a motor configured to selectively operating the rod feeding subassembly, the brake subassembly, and the bending subassembly (Block 1204). The operations 1200 further include retaining a surgical rod in the rod feeding subassembly (Block 1206), causing a feeding actuator of the rod feeding subassembly to selectively move the surgical rod in a direction parallel to a longitudinal axis of the surgical rod (Block 1208), and causing the feeding actuator to selectively rotate the surgical rod about the longitudinal axis of the surgical rod (Block 1210).

The operations 1200 further include receiving the surgical rod in the brake feeding subassembly from the rod feeding subassembly (Block 1212), and causing a brake actuator of the brake subassembly to selectively fix a first portion of the surgical rod with respect to the brake subassembly (Block 1214). The operations 1200 further include causing a bending actuator of the bending subassembly to selectively rotate about a first rotational axis perpendicular to the longitudinal axis of the surgical rod, wherein rotating the bending actuator causes the bending actuator to engage a second portion of the rod and bend the second portion of the rod with respect to the first portion of the surgical rod so that the first portion and the second portion of the surgical rod define a first bend angle. The operations 1200 further include causing a blade of the brake subassembly to selectively cut the surgical rod.

Additional operations may include data acquisition, which may occur prior to rod bending and after screws are properly placed via a camera system, which may send the data to the bending robot. Based on the data, the bending robot may perform the operations described above. In another embodiment, the data for bend points can be received through an acquisition camera and a probe that is tracked by the camera, where the probe is touched on the head of each of a plurality of pedicle screws after they have been placed on the patient's spine. Those points can be used to generate a curve that can be modified and fine-tuned by the surgeon, and that can be used to generate bend points, which can be used by the bending robot to make appropriate bends in the surgical rod. In another example, an intra-operative robot used for screw placement can be used to determine the coordinates of the pedicles and hence can be used to generate a bend curve. In some embodiments, preoperative planning software, such as Surgimap or GMAP, for example, can be used to configure the bend points, which can then be used by the bending robot to bend the surgical rod. Data from the camera may also be used to verify that the robot is operating correctly and/or within predetermined tolerances, and may generate data to instruct the robot to correct for errors in real time.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A method of using a robotic system for automatically bending a surgical rod, comprising:
   providing a surgical rod in the robotic system; and
   bending the surgical rod,
   wherein the robotic system includes:
      a robot base;
      rod feeding subassembly coupled to the robot base, the rod feeding subassembly comprising a feeding actuator configured to retain the surgical rod therein, and selectively move the surgical rod in a direction parallel to a longitudinal axis of the surgical rod;
      a brake subassembly coupled to the robot base, the brake subassembly including a brake actuator configured to receive the surgical rod from the rod feeding subassembly, and selectively fix a first portion of the surgical rod with respect to the brake subassembly; and
      a bending subassembly coupled to the robot base, the bending subassembly comprising a bending actuator configured to selectively rotate about a first rotational axis perpendicular to the longitudinal axis of the surgical rod, wherein rotating the bending actuator causes the bending actuator to engage a second portion of the surgical rod and bend the second portion of the surgical rod with respect to the first portion of the surgical rod so that the first portion and the second portion of the surgical rod define a first bend angle,
   wherein the brake subassembly further includes:
      a motor; and
      a brake actuator linkage co pied between the motor and the brake actuator, wherein the brake actuator linkage is configured to transfer power from the motor to the brake actuator to selectively fix the first, portion of the surgical rod with respect to the brake subassembly.

2. The method of claim 1, wherein the rod feeding subassembly further includes:
   a motor; and
   a feeding actuator linkage coupled between the motor and the feeding actuator, wherein the feeding actuator linkage is configured to transfer power from the motor to the feeding actuator to selectively move the surgical rod in the direction parallel to the longitudinal axis of the surgical rod.

3. The method of claim 2, wherein the feeding actuator is further configured wherein the feeding actuator linkage is further configured to transfer power from the motor to the feeding actuator to selectively rotate the surgical rod about the longitudinal axis of the surgical rod.

4. The method of claim 3, wherein the motor comprises a first motor and a second motor,
   wherein the feeding actuator linkage comprises a first feeding actuator linkage coupled between the first motor and the feeding actuator and a second feeding actuator linkage coupled between the second motor and the feeding actuator,
   wherein selective operation of the first motor in a first rotational direction and selective operation of the second motor in a second rotational direction causes the first feeding actuator linkage and the second feeding actuator linkage to move the surgical rod in a first longitudinal direction parallel to the longitudinal axis of the surgical rod.

5. The method of claim 4, wherein selective operation of the first motor in a third rotational direction opposite the first rotational direction and selective operation of the second motor in a fourth rotational direction opposite the second rotational direction causes the first feeding actuator linkage and the second feeding actuator linkage to move the surgical rod in a second longitudinal direction opposite the first longitudinal direction.

6. The method of claim 5, wherein selective operation of the first motor in the first rotational direction and selective operation of the second motor in the fourth rotational direction causes the first feeding actuator linkage and the second feeding actuator linkage to rotate the surgical rod in a fifth rotational direction.

7. The method of claim 6, wherein selective operation of the first motor in the third rotational direction and selective operation of the second motor in the second rotational direction causes the first feeding actuator linkage and the second feeding actuator linkage to rotate the surgical rod in a sixth rotational direction opposite the fifth rotational direction.

8. The method of claim 1, wherein the brake subassembly further includes a blade configured to selectively cut the surgical rod.

9. The method of claim 8, wherein the brake actuator linkage is further configured to transfer power from the motor to the blade to selectively cut the surgical rod.

10. The method of claim 9, wherein selective operation of the motor in a first rotational direction when the brake actuator is in a neutral position causes the brake actuator linkage to move the brake actuator from the neutral position to an engaged position to selectively fix the first portion of the surgical rod with respect to the brake subassembly, and
wherein selective operation of the motor in a second rotational direction opposite the first rotational direction when the brake actuator is in the engaged position causes the brake actuator linkage to move the brake actuator from the engaged position to the neutral position to selectively release the first portion of the surgical rod with respect to the brake subassembly.

11. The method of claim 10, wherein selective operation of the motor in the second rotational direction when the brake actuator is in the neutral position causes the blade to cut the surgical rod.

12. The method of claim 1, wherein the bending subassembly further includes:
a motor; and
a bending actuator linkage coupled between the motor and the bending actuator, wherein the bending actuator linkage is configured to transfer power from the motor to the bending actuator to selectively rotate the bending actuator about the first rotational axis and bend the second portion of the surgical rod with respect to the first portion of the surgical rod.

13. The method of claim 12, wherein the bending actuator comprises a roller bearing configured to engage the second portion of the surgical rod, wherein movement of the second portion of the surgical rod during bending causes the roller to rotate about a second rotational axis parallel to the first rotational axis.

14. The method of claim 1, wherein the feeding actuator is further configured to:
after the bending actuator bends the second portion of the surgical rod with respect to the first portion of the surgical rod, selectively move the surgical rod in the direction parallel to the longitudinal axis of the surgical rod, and
selectively rotate the surgical rod about the longitudinal axis of the surgical rod, wherein the brake actuator is further configured to:
selectively fix a third portion of the surgical rod with respect to the brake subassembly, and
wherein the bending actuator is further configured to:
selectively rotate about the first rotational axis perpendicular to the longitudinal axis of the surgical rod, and
selectively rotate about the first rotational axis to bend the first portion of the surgical rod with respect to the third portion of the surgical rod so that the third portion and the first portion of the surgical rod define a second bend angle.

15. The method of claim 1, further comprising a first housing comprising:
a transmission input;
a first transmission subassembly coupled between the transmission input and the feeding actuator;
a second transmission subassembly coupled between the transmission input and the brake actuator; and
a third transmission subassembly coupled between the transmission input and the bending actuator; and
a second housing comprising:
a motor; and
a transmission output configured to selectively operate in response to operating the motor,
wherein the first housing is configured to engage with the second housing to couple the transmission output of the second housing to the transmission input of the first housing, wherein selectively operating the transmission output causes the transmission input to selectively transfer power from the motor to the feeding actuator, the brake actuator, and the bending actuator.

16. The method of claim 15, wherein the first housing is configured to be selectively removable from the second housing.

17. The method of claim 1, the robotic system further includes:
a processor circuit; and
a memory coupled to the processor circuit, the memory comprising machine-readable instructions that, when executed by the processor circuit, cause the processor circuit to:
cause the rod feeding subassembly to selectively move the surgical rod;
cause the brake subassembly to selectively fix the first portion of the surgical rod; and
cause the bending subassembly to selectively rotate about the first rotational axis to engage the second portion of the surgical rod and bend the second portion of the surgical rod with respect to the first portion of the surgical rod.

18. A method of operating a robotic system comprising:
retaining a surgical rod in a rod feeding subassembly, and causing a feeding actuator of the rod feeding subassembly to move the surgical rod;
operating a brake subassembly by receiving the surgical rod in the brake feeding subassembly from the rod feeding subassembly;
causing a brake actuator of the brake subassembly to selectively fix a first portion of the surgical rod with respect to the brake subassembly;
operating a bending subassembly by causing a bending actuator of the bending subassembly to selectively rotate about a first rotational axis perpendicular to the longitudinal axis of the surgical rod, wherein rotating the bending actuator causes the bending actuator to engage a second portion of the rod and bend the second portion of the rod with respect to the first portion of the surgical rod so that the first portion and the second portion of the surgical rod define a first bend angle,
wherein the brake subassembly further includes:
a motor; and
a brake actuator linkage coupled between the motor and the brake actuator, wherein the brake actuator linkage is configured to transfer power from the motor to the brake actuator to selectively fix the first portion of the surgical rod with respect to the brake subassembly.

19. The method of claim 18, further comprising, prior to selectively operating the rod feeding subassembly, sterilizing a first housing comprising the rod feeding subassembly, the brake subassembly, and the bending subassembly; and
removably coupling the first housing to a second housing comprising a motor configured to perform the selectively operating the rod feeding subassembly, selectively operating the brake subassembly, and selectively operating the bending subassembly.

* * * * *